United States Patent [19]

Ebata et al.

[11] Patent Number: 4,497,797

[45] Date of Patent: Feb. 5, 1985

[54] β-GALACTOSIDASE INHIBITOR GT-2558 AND ITS DERIVATIVES

[75] Inventors: Mitsuo Ebata; Yukio Miyake; Yoshimi Kawamura, all of Osaka, Japan

[73] Assignee: Shionogi & Co., Ltd., Osaka, Japan

[21] Appl. No.: 393,506

[22] Filed: Jun. 29, 1982

Related U.S. Application Data

[63] Continuation-in-part of Ser. No. 311,326, Oct. 14, 1981, abandoned.

[30] Foreign Application Priority Data

Oct. 27, 1980 [JP] Japan .................................. 55-150927

[51] Int. Cl.³ .......................... A61K 35/00; C12P 1/06
[52] U.S. Cl. .................................... 424/118; 424/116; 435/169

[58] Field of Search ................. 424/116, 118; 435/169

[56] References Cited

U.S. PATENT DOCUMENTS 3,978,210 8/1976 Mizuno et al. ...................... 424/118
3,991,183 11/1976 Celmer et al. ...................... 424/118

Primary Examiner—Jerome D. Goldberg
Attorney, Agent, or Firm—Wenderoth, Lind & Ponack

[57] ABSTRACT

β-Galactosidase inhibitors GT-2558, GT-2558-A, and GT-2558-B produced by a strain *Streptomyces lydicus* PA-5726, and their derivatives, acetyl-GT-2558-A and acetyl-GT-2558-B, useful as diagnostatic aid in β-galactosidase deficiency, used in purification of enzymes, in research of new β-galactosidase, in controlling sweetness of lactose-containing foods and in fermentation industry.

4 Claims, 4 Drawing Figures

4,497,797

β-GALACTOSIDASE INHIBITOR GT-2558 AND ITS DERIVATIVES

This application is a continuation-in-part of application Ser. No. 311,326, filed Oct. 14, 1981 (now abandoned).

BACKGROUND OF THE INVENTION

It has been reported by H. B. Bosmann [Biochem. Biophys. Acta. 264, 339 (1972)] that glucosidase activity, particularly, β-galactosidase activity is elevated in 3T3 fibroflast cells transformed by RNA tumor virus. In this connection, various researches have been made and described in, e.g., Jap. Pat. Publication No. 53-31238; The Journal of Antibiotics 28, 1006 (1975); ibid. 32 (3), 212 (1979); and ibid. 32 (3), 217 (1979). The present inventors have also investigated intensively to find the substances having β-galactosidase inhibitory activity, and as the result, they have found novel β-galactosidase inhibitor GT-2558 in the culture broth resulted from a strain of certain microorganisms and accomplished this invention.

SUMMARY OF THE INVENTION

The present invention relates to novel β-galactosidase inhibitor GT-2558 and its derivatives, and a method for producing them.

The β-galactosidase inhibitor GT-2558 in the present invention is a mixture of A, B, and other minor components and can be separated into GT-2558-A and GT-2558-B in a conventional manner. Additionally these compounds may be stabilized by acetylation. The properties of GT-2558, GT-2558-A and B, and their acetyl derivatives are shown as follows. The present invention includes not only these compounds per se but also the pharmaceutically acceptable salts of these compounds.

(1) GT-2558
  a. Nature
     Weakly basic powder
  b. Solubility
     Freely soluble in water, soluble in methanol, acetic acid, and pyridine, slightly soluble in ethanol and propanol, and insoluble in acetone, ether, ethyl acetate, chloroform, and benzene.
  c. Color reaction
     Ninhydrin reaction test positive
     Silver mirror test positive
     Tollens reaction test (with yellow phloroglucinol and hydrochloric acid)
  d. UV
     No characteristic absorption
  e. TLC on a silica gel plate
     $R_f = 0.29$ (developed with acetonitrile:acetic acid:water = 5:1:2)
  f. Specific β-galactosidase inhibitory activity
     55,000 IU/mg ($IC_{50}$ 0.0045 mcg)

Figure 1:
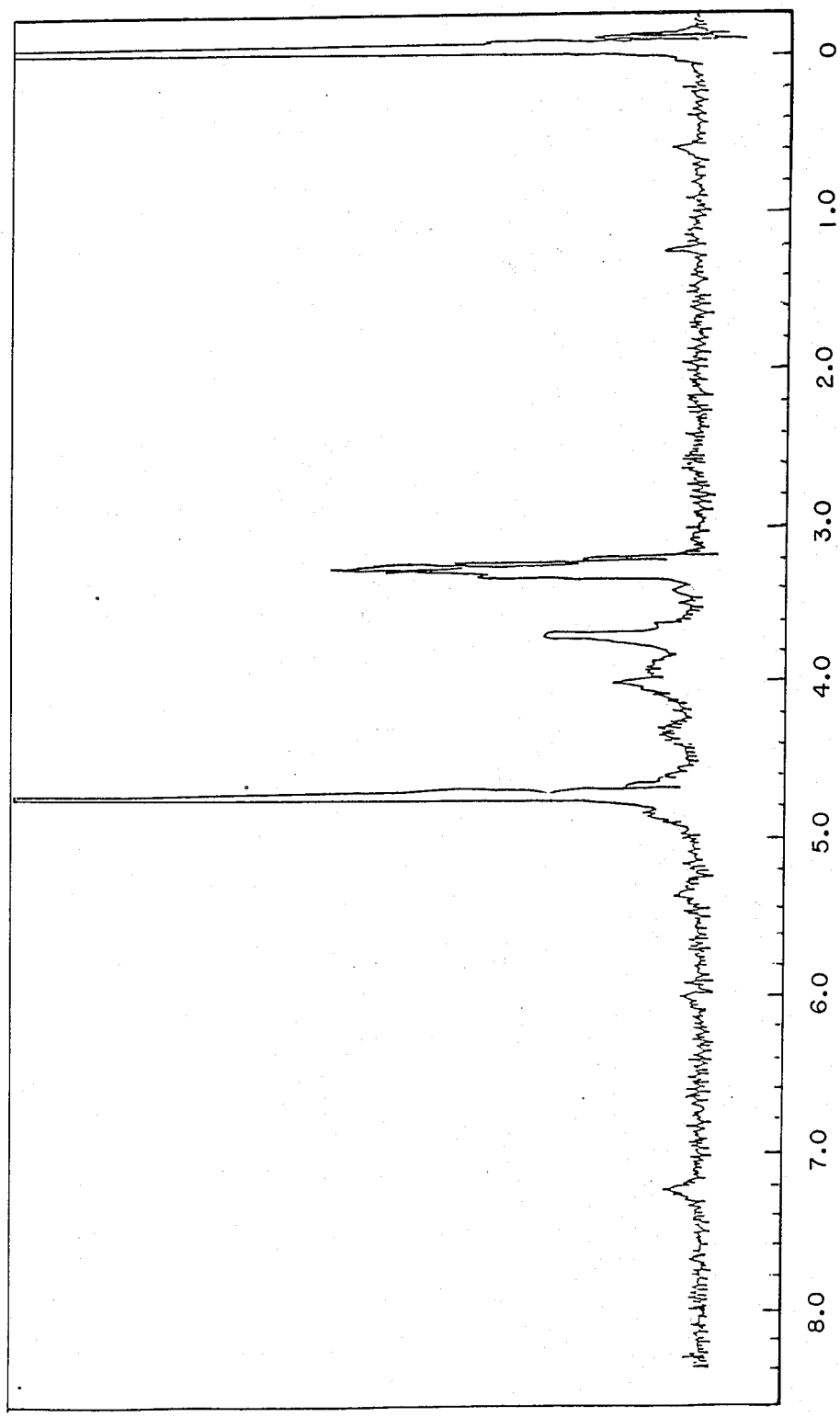
FIG. 1 and FIG. 2 show the NMR spectrums of the GT-2558-A measured in heavy methanol and $d_5$-pyridine respectively.
Figure 2:
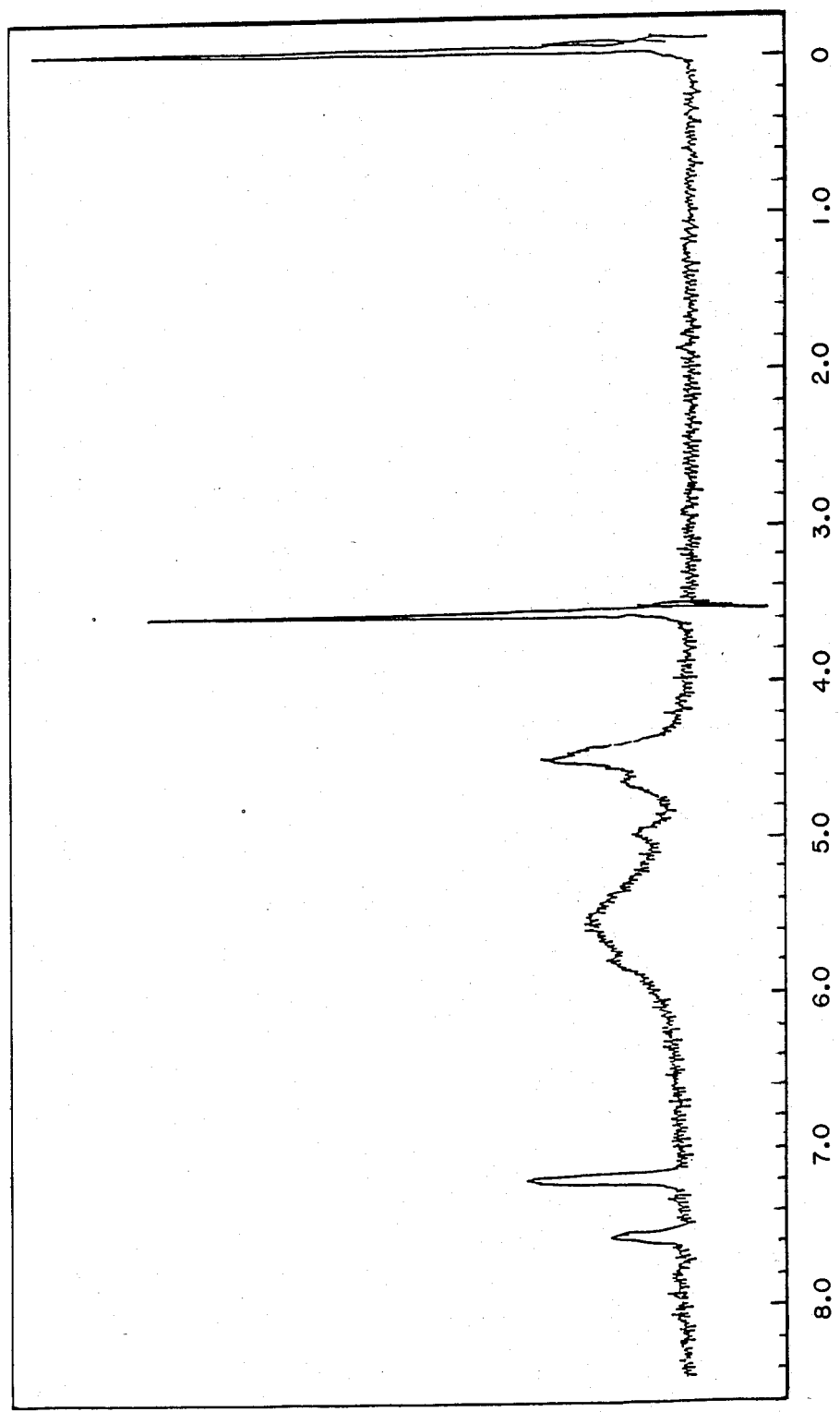

(2) GT-2558-A
  a. m.p.
     106°–108° C.
  b. Molecular weight (mass spectrum)
     Maximum mass m/e = 302
  c. Elemental analysis
     Found. C,41.34; H,6.16; N,7.43; O, 45.06 (%)
  d. IR
     $\nu_{max}^{KBr}$ 3400, 2900, 1640, 1565, 1505, 1455, 1415, 1360, 1300, 1270, 1160, 1110, 1075, 1035, 955, 930, 890, 855, 795 cm$^{-1}$.
  e. NMR
     FIG. 1 and FIG. 2
  f. β-Galactosidase inhibitory activity

| Enzyme | pH at | Origin | $IC_{50}$ | |
|---|---|---|---|---|
| Taka β-galactosidase | 5.0 | Aspergillus oryzae(Sankyo) | 0.0018 | mcg |
| Taka β-galactosidase | 4.5 | Aspergillus oryzae(Sankyo) | 0.0045 | |
| Galantase | 4.5 | Aspergillus oryzae(Tokyo Tanabe) | 0.0045 | |
| Bovine β-galactosidase | 7.2 | Bovine liver (Sigma) | 26.6 | | g. Specific β-galactosidase inhibitory activity
     136,700 IU/mg ($IC_{50}$ 0.0018 mcg)

(3) Acetyl-GT-2558-A
  a. Nature
     Colorless fine crystals (recrystallized from benzene-methanol)
  b. Solubility
     Soluble in methanol, ethanol, chloroform, dioxane, and water, slightly soluble in ethyl acetate, and insoluble or hardly soluble in carbon tetrachloride and benzene.
  c. Color reaction
     Ninhydrin reaction test positive
     Ammoniac silver nitrate reaction test positive
  d. m.p. and decom.p.
     m.p. 41° C.; decomp.p. 149°–153° C.
  e. Specific rotation
     $[\alpha]_D^{24} + 29.6°$ (c 1.0 methanol)
  f. Molecular weight (mass spectrum)
     Maximum mass m/e = 491 (M+1)
  g. Elemental analysis
     Found. C,51.30; H,6.27; N,5.65; O,36.78 (%)
  h. UV
     No characteristic absorption
  i. IR
     $\nu_{max}^{KBr}$ 3430, 2920, 1745, 1630, 1435, 1390, 1370, 1245, 1090, 1040, 820, 760 cm$^{-1}$.

(4) Acetyl-GT-2558-B
  a. Nature
     Colorless fine crystals (recrystallized from ethyl acetate-methanol)
  b. Solubility
     Soluble in methanol, ethanol, and water, slightly soluble in ethyl acetate and chloroform, and insoluble or hardly soluble in carbon tetrachloride and benzene.
  c. Color reaction
     Ninhydrin reaction test positive
     Ammoniac silver nitrate reaction test positive
  d. m.p. and decomp.p.
     m.p. 76°–78° C.; decomp.p. 161°–163° C.
  e. Specific rotation
     $[\alpha]_D^{24} + 13.8°$ (c 1.0 methanol)
  f. Molecular weight (mass spectrum)

Figure 3:
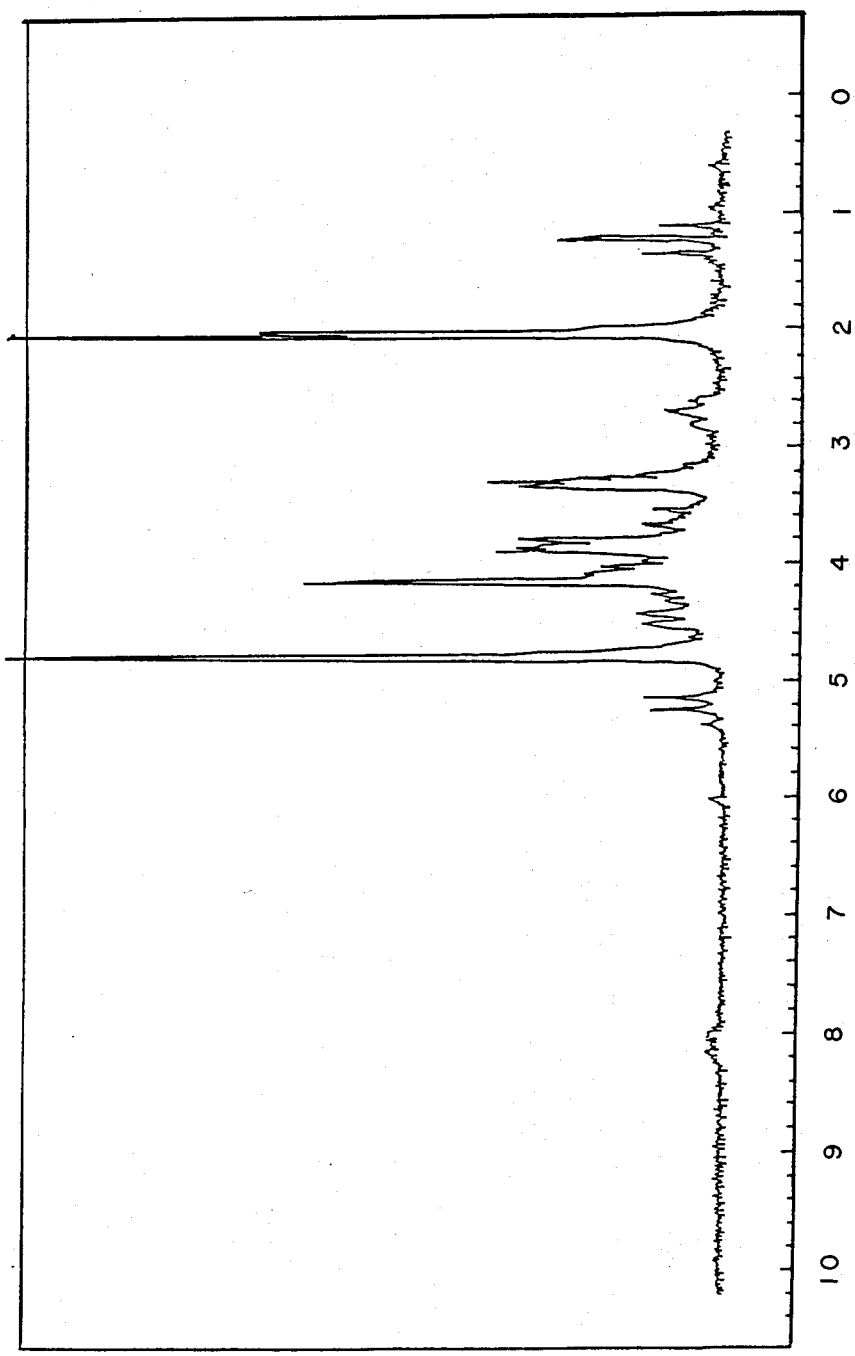
FIG. 3 shows the NMR spectrum of the acetyl-GT-2558-B measured in heavy methanol.

Maximum mass m/e=429 (M+1)

g. Elemental analysis
   Found. C,46.58; H,6.58; N,6.56; O,38.51 (%)
h. UV
   No characteristic absorption
i. IR
   $\nu_{max}^{KBr}$ 3410, 2930, 2735, 2360, 1640, 1550, 1435, 1380, 1245, 1195, 1115, 1090, 1045, 875, 815 cm$^{-1}$.
j. NMR
   FIG. 3
k. Specific β-galactosidase inhibitory activity
   1,640 IU/mg (IC$_{50}$ 0.15 mcg)

The β-galactosidase inhibitory activity and the specific β-galactosidase inhibitory activity shown in the above properties are observed by means of colorimetric determination of o-nitrophenol which is liberated on hydrolysis of the substrate o-nitrophenyl β-D-galactopyranoside catalyzed by β-galactosidase. In this connection, to a solution (0.25 ml) of β-galactosidase dissolved in 0.1M acetic acid buffer (pH 5.0), a solution (0.25 ml) containing test compounds is added, incubated at 30° C. for 10 minutes, and mixed with 0.01M substrate solution (0.5 ml) of o-nitrophenyl β-D-galactopyranoside dissolved in the above buffer. The mixture is incubated at 30° C. for 15 minutes, the reaction is stopped by the addition of 1M sodium carbonate (1 ml), the total volume is adjusted to 10 ml by addition of water (8 ml), and then the absorbance (A) at 420 nm is measured. Concurrently the absorbance (B) of the control prepared with only the buffer not containing the above test compounds is measured, and the inhibitory rate is calculated from (B-A)/B×100. Wherein β-galactosidase prepared from Taka-diastase (trade name, Sankyo Co.) is employed. One unit of inhibitory activity (1 IU) is defined as the amount of a test compound required for 50% inhibition (IC$_{50}$) of the β-galactosidase activity in the above condition.

The GT-2558 seems to be a novel β-galactosidase inhibitor since the properties are different from the known β-galactosidase inhibitors. As an organism which produces the said GT-2558, the strain of PA-5726 which was isolated from the soil sample collected in Nakadori Island, Minami-Matsuura District, Nagasaki Pref., Japan is shown.

This strain was determined to be a strain of *Streptomyces lydicus* classificationally, and the strain of PA-5726 has been deposited as *Streptomyces lydicus* PA-5726, FERM-BP61 in Agency of Industrial Science & Technology, Ibaraki, Pref., Japan, and as ATCC No. 31975 at American Type Culture Collection, Rockville, Md. U.S.A.

The taxonomical properties of the said strain are shown as follows.

(a) Morphological characteristics (Bennett's agar, cultured at 28° C. for 14 days)

Neither sporangium, flagellated spore, nor sclerotium is observed, and no split by fragmentation in substrate hyphae is observed. On this medium, it forms abundant aerial hyphae which develop into many spirals. The surface structure of the spore is smooth under the electron microscopic observation. In this strain, with the lapse of time the surface of the colony is moistened to become so-called hygroscopic and change into black.

(b) Cultural views on various media (cultured at 28° C. for 14 days)

Expression of color is in accordance with "Guide to Color Standard" (Japan Color Institute ed.).

| Media | Growth | Aerial Hyphae Formation | Aerial Hyphae Color | Color of Substrate Hyphae | Soluble Pigment |
|---|---|---|---|---|---|
| Sucrose. Nitrate Agar | fair | no | — | pale yellowish brown | no |
| Glucose. Asparagine Agar | " | fair | light brownish gray | pale yellowish brown | " |
| Glycerin. Asparagine Agar | good | good | light brownish gray | pale yellowish brown | " |
| Inorganic salt. | " | " | brownish gray* | pale yellowish brown | " |
| Starch Agar Tyrosine Agar | " | " | light brownish gray | yellowish brown | " |
| Nutrient Agar | " | no | — | yellowish brown | " |
| Yeast extract. Malt extract Agar | " | good | brownish gray* | yellowish brown | " |
| Oatmeal Agar | " | " | brownish gray* | pale yellowish brown | " |
| Bennett's Agar | " | " | brownish gray* | yellowish brown | " |

*The surface of the colony is moistened to become so-called hygroscopic and change into black.

Growth temperature (Bennett's agar, cultured at each temperature for 2 weeks. The growth at 10° C. was observed also 3 weeks after.)

10° C.:
Observed for 2 weeks, scarcely growth.
Observed for 3 weeks, good growth forming aerial hyphae fairly.

28° C.:
Growth, formation of aerial hyphae, and formation of spore each is good.

37° C.: No growth.
45° C.: No growth.

(c) Physiological properties (cultured at 28° C. for 14 days)

| | |
|---|---|
| Liquefaction of gelatin | positive |
| Production of melanoid pigment | negative |
| Tyrosinase reaction | negative |
| Peptonization of milk | positive |
| Coagulation of milk | positive |
| Hydrolysis of starch | positive |

(d) Utilization of carbon source
Sugar much required for growth
L-arabinose, D-xylose, D-glucose, D-fructose, sucrose, inositol, raffinose, and D-mannitol
Sugar slightly concerning for growth
L-rhamnose From the above description of various properties, it is obvious that this strain belongs to the genus Streptomyces. In Waksman's "The Actinomycetes" vol. 2 (1961), Shirling and Gottlieb's "International Streptomyces Project" report, ["International Journal of Systematic Bacteriology" vol. 18 p.69 and p.279 (1968), ibid. vol. 19 p.391 (1969), ibid. vol. 22 p.265 (1972)], "Bergey's Manual of Determinative Bacteriology" 8th Edition (1974), and other publications as to new species of actinomycetes, the species closely related to the strain of PA- 5726 were searched, and *Streptomyces lydicus* [International Journal of Systematic Bacteriology vol. 19, p.448 (1969), Bergey's Manual of Determinative Bacteriology 8th Edition, p.772 & p.777 (1974), and U.S. Pat. No. 3,160,560 (1964)] was shown as the most closely related species. As a result of comparing the various properties of the strain PA-5726 with those of *Streptomyces lydicus* described in these publications, good agreements were obtained. Therefore the strain PA-5726 was determined to be a strain belonging to the same species as *Streptomyces lydicus* and named *Streptomyces lydicus* PA-5726.

In the present invention not only the strain PA-5726 and its natural and artificial variants but also all of the strains which belong to *Streptomyces lydicus and product GT-2558*, can be used and are within the scope of this invention.

Production of GT-2558 comprises culturing a GT-2558 producing strain on a nutrious medium under aerobic conditions and recovering GT-2558 from the culture broth after cultivation. General prodedure for producing GT-2558 is described in the followings.

Referring to medium components and culture conditions, the conventional ones employed in producing antibiotics may be employed. The medium contains essentially carbon sources, nitrogen sources, inorganic salts, etc. If necessary, vitamines, precursors, etc. may be added. As carbon sources, for example, glucose, starch, dextrin, glycerin, molasses, and organic acid are employed alone or as a mixture. As nitrogen sources, for example, soybean meal, corn steep liquor, meat extract, yeast extract, cotton seed meal, peptone, wheat embryo, ammonium sulfate, and ammonium nitrate are employed alone or as a mixture. As inorganic salts, for example, calcium carbonate, sodium chloride, potassium chloride, magnesium sulfate, cobaltous chloride, and various phosphates may be added to the medium, if necessary.

The cultivation may be conducted in a conventional manner employed in producing antibiotics, preferably in liquid media or under submerged aerial conditions in case of a large scale production. If a change of the medium pH occurs, a buffer such as calcium carbonate may be added to the medium. The cultivation is conducted preferably at 20°–40° C., and particularly at 25°–32° C. The cultivation time is altered fairly according to the fermentation scale; e.g., about 20–80 hours are required as cultivation time in a large scale production. If vigorous foaming occurs during the cultivation, for example, antifoaming agents such as vegetable oil, lard, and polypropylene glycol may be added suitably before or during the cultivation.

After termination of the cultivation a conventional manner for recovering the fermentation products may be used properly in recovering GT-2558 from the culture broth. For example, filtration, centrifugal separation, adsorption-desorption procedure and chromatography with various ion-exchange resins and other adsorbents, and extraction with various organic solvents may be employed in proper combination preferably. Additionally the acetyl derivative of GT-2558 can be separated as a means for purification. To obtain the acetyl derivative crude powder of GT-2558 is dissolved in acetic acid, the excess amount of acetic anhydride is added thereto, and the mixture may be allowed to react at room temperature under stirring. In this connection, in order to prevent decomposition of GT-2558, if desired, it may be considered to use a suitable stabilizer in the separating step.

Occasionally it is preferred that GT-2558 is changed into the salts for convenience in separating procedure and medical application to human and animals. The acids which can form the salts together with GT-2558 are inorganic acids such as hydrochloric acid, hydrobromic acid, hydroiodic acid, sulfuric acid, nitric acid, phosphoric acid, and carbonic acid, and organic acids such as acetic acid, fumaric acid, malic acid, tartaric acid, maleic acid citric acid, mandelic acid, ascorbic acid, and gallic acid.

As shown in the above, GT-2558 is a mixture of A, B, and other minor components, and so GT-2558 may be separated into each of these components if desired. As a means for separation, e.g., various chromatographic means and gel filtration are employed. Acetylation and formation of salts mentioned above may also be used.

GT-2558, its components and acetyl derivatives, and the pharmaceutically acceptable salts thereof can be used as reagents for determination of $\beta$-galactosidase activity, acting as $\beta$-galactosidase inhibitors. These compounds together with conventional types of diluents, stabilizers, preservatives, moistening agents, and surface active agents can be administered orally as tablets, capsules, and powders, or parenterally as injections, liniments, and suppositories, and the dosage is changeable according to therapeutic purpose, the age, and conditions of a patient, etc.

GT-2558 and its derivatives can also be used in controlling sweetness of lactose-added foods and drinks in which lactose is used in place of sucrose, for example, dairy products, confectionary, fruit juices. In order to sweeten the foods and drinks by addition of lactose, the lactose added is hydrolyzed with $\beta$-galactosidase to give glucose and galactose which afford sweetness to the foods and drinks. It is appropriate, however, to control the sweetness by suppressing hydrolysis of lactose at a pre-fixed stage with addition of a $\beta$-galactosidase inhibitor, GT-2558 or its derivatives. Examples 19 and 20 as shown below illustrate more in detail the method of controlling sweetness of milk and dry skim milk.

The following examples serve to illustrate the processes for producing a group of the GT-2558 compounds, but are not intended to limit the scope of the invention.

EXAMPLE 1

Each 100 ml of the medium, (pH 7.0) containing glucose (1.0%), casamino acid (0.2%), yeast extract (0.2%), and meat extract (0.1%) is placed in 500 ml shaking flasks and sterilized at 120° C. for 20 minutes, and the thus obtained media are used for seed culture.

The platinum loop of the slant culture resulting from a strain of *Streptomyces lydicus* PA-5726, FERM-BP61 is inoculated on the above media for seed culture, and cultured under shaking at 28° C., 140 reciprocations per minute, and 7 cm amplitude for 2 days to give the seed mash.

On the other hand, lard (0.1%) is added to a medium (pH 7.0) containing glycerin (4.0%), meat extract (1.5%), peptone (1.5%), KCl (0.076%), $MgCl_2.6H_2O$ (0.042%), $FeCl_3.6H_2O$ (0.00245%), $ZnSO_4.7H_2O$ (0.00219%), and $MnCl_2.4H_2O$ (0.00181%). This medium (80 ml each) is placed in 500 ml shaking flasks and sterilized at 120° C. for 20 minutes. The thus obtained medium is used as main fermentation medium, and the above seed mash is inoculated on the fermentation medium at 2% content and cultured under shaking at 28°

C., 140 reciprocations per minute, and 7 cm amplitude for 6 days.

In this culture broth the $\beta$-galactosidase inhibitor GT-2558 (48,100 IU/mg, $IC_{50}=0.0052$ mcl) is accumulated.

EXAMPLE 2

In the same manner as in Example 1, main fermentation medium (8 L) is employed in cultivation and immediately after termination of the cultivation the organism is separated by centrifugal separation to yield a clear filtrate (6.3 L).

This filtrate is adjusted at pH 4.5 by addition of hydrochloric acid, and active carbon (1.5%, 94.5 g) is added thereto on which pigments and impurities are absorbed under stirring for 30 minutes, and filtered with assistance of Celite to give a clear filtrate (6.9 L).

This filtrate is passed through 2 L of a strongly basic anion-exchange resin Dowex-1×8 (OH type) (trade name, Dow Chemical Co.) to remove anionic substances. The resultant solution is furthermore passed through a column of 1 L of a strongly acidic cation-exchange resin Dowex—50W×8 (H type), on which GT-2558 is adsorbed, washed with water sufficiently, and then eluted with 0.5N hydrochloric acid.

The eluted fractions with the $\beta$-galactosidase inhibitory activity are collected and immediately neutralized by removal of excess Cl-ion with a weakly basic anion-exchange resin Amberlite IRA-47 (OH type) (trade name, Rohm & Haas Co.) to give a GT-2558 solution (400 ml). The $\beta$-galactosidase inhibitory activity of this solution is 454,500 IU/ml ($IC_{50}=0.00055$ mcl).

EXAMPLE 3

The GT-2558 solution obtained in Example 2 is condensed by means of lyophilization to give a yellowish brown oily substance, which is dissolved in a small amount of 80% methanol. The residue is filtered and acetone (10 times in volume) is added to the filtrate to yield the precipitate, from which supernatant solution of acetone is removed by centrifugal separation.

The precipitate is dissolved in a small amount of methanol again and ethyl acetate (5–10 times in volume) is added thereto gradually to yield the precipitate, which is collected by filtration and dried to give pale yellow crude powder of GT-2558 (8,090 mg). The $\beta$-galactosidase inhibitory activity of this crude powder is 20,000 IU/mg ($IC_{50}=0.013$ mcg) and in the above procedure this substance is obtained in yield of more than 50%.

EXAMPLE 4

The crude powder (800 mg) obtained in Example 3 is dissolved in a small amount of 80% methanol, applied to a column (2.6∅×100 cm) of a weakly basic anion-exchange resin Amberlite IRA-47 (OH type) in 80% methanol, and eluted with the same 80% methanol as a developer. The eluate is collected as 6 g each fractions, the $\beta$-galactosidase inhibitory activity is detected in Nos. 53–90 fractions, and the active fractions are combined and condensed under reduced pressure to give pale yellowish powder (262 mg). The inhibitory activity of this crude powder is 35,600 IU/mg ($IC_{50}=0.007$ mcg) and the yield is 58.3%.

EXAMPLE 5

The crude powder (400 mg) obtained in Example 4 is furthermore dissolved in 80% methanol, applied to a column (3.1∅×130 cm) of Sephadex LH-20 (trade name, Pharmacia Fine Chemical Co.) equilibrated with 80% methanol, and eluted with the same 80% methanol as a developer. The elute is collected as 4 g each fractions, and the $\beta$-galactosidase inhibitory activity is detected in Nos. 125–135 fractions. The active fractions are combined and condensed under reduced pressure to give colorless powder (214 mg). The inhibitory activity of this crude powder is 55,000 IU/mg ($IC_{50}=0.0045$ mcg) and the yield is 82.7%.

EXAMPLE 6

The crude powder (135 mg) obtained in Example 5 is dissolved in a small amount of 0.2N pyridine-acetic acid buffer solution, applied to a column (2∅×72 cm) of a strongly acidic cation-exchange resin Dowex-50 W×8 equilibrated sufficiently with the same buffer solution, and eluted with the same buffer solution as a developer. The eluate is collected in every 7 g fractions, and the $\beta$-galactosidase inhibitory activity is detected in Nos. 122–138 fractions and in Nos. 141–160 fractions respectively. Named GT-2558-A and B in order of elution, the yields are 37.2% (A) and 18.3% (B). The fractions are condensed under reduced pressure separately to give light yellow powder (37 mg) of the GT-2558-A whose inhibitory activity is 73,500 IU/mg ($IC_{50}=0.0034$ mcg) and brown powder (54 mg) of the GT-2558-B whose inhibitory activity is 24,500 IU/mg ($IC_{50}=0.010$ mcg).

EXAMPLE 7

The GT-2558-A powder (57 mg) obtained in Example 6 is dissolved in a small amount of 70% ethanol, applied to a column (2.6∅×95 cm) of Sephadex LH-20 equilibrated with 70% ethanol, and eluted with the same 70% ethanol as a developer.

Each fraction (3 g) of the eluate is collected, and the $\beta$-galactosidase inhibitory activity is detected in Nos. 80–95 fractions. The active fractions are combined and condensed under reduced pressure to give colorless powder (32.6 mg) whose inhibitory activity as 117,800 IU/mg ($IC_{50}=0.0021$ mcg). This colorless powder is recrystallized from a small amount of a mixture of solvents (isopropanol-ethanol) repeatedly to give colorless fine crystals (19.4 mg) of the GT-2558-A. The inhibitory activity of this product is 136,700 IU/mg ($IC_{50}=0.0018$ mcg).

EXAMPLE 8

The crude powder (500 mg) of GT-2558 ($IC_{50}=0.007$ mcg) obtained in Example 4 is dissolved in acetic acid (10 ml) under ice-cooling, allowed to warm up to room temperature under stirring after addition of acetic anhydride (10 ml), and acetylated by further addition of acetic anhydride (10 ml). The reaction is carried out at room temperature for 2 hours and terminated on addition of alcohol. The mixture is condensed under reduced pressure in the presence of toluene to give a yellow oily substance of the actyl-GT-2558. This substance is checked by means of thin layer chromatography on a silica gel plate with hexane-chloroform-methanol (30:30:12) as the solvent system, and as the result, the acetyl-GT-2558-A is recognized at 0.40 ($R_f$ value) and the acetyl-GT-2558-B at 0.05 ($R_f$ value).

EXAMPLE 9

The yellow oily substance of the acetyl-GT-2558 obtained in Example 8 is dissolved in a small amount of methanol, applied to a column (1.7∅×40 cm) of silica gel (50 g) equilibrated with hexane-chloroform-methanol (30:30:15) as the solvent system, and eluted with the same solvent system (40 ml) and successively with the solvent system of hexane-chloroform-methanol (30:30:20). Each fraction (5 g) of the eluate is collected, and checked by thin layer chromatography on a silica gel plate, which indicates that the acetyl-GT-2558-A is eluted in Nos. 30–42 fractions and the acetyl-GT-2558-B in Nos. 115–210 fractions. The fractions are combined respectively and condensed under reduced pressure to give the acetyl-GT-2558-A and B as a yellow oily substances respectively.

EXAMPLE 10

The yellow oily substance of the acetyl-GT-2558-A obtained in Example 9 is chromatographed for purification repeatedly on a silica gel column, in which the solvent system of hexane-chloroform-methanol (30:30:6) is employed, to give a transparent colorless oily substance. Thus obtained substance is dissolved in a small amount of methanol and recrystallized from a mixture of benzene and methanol to give colorless fine crystals of the acetyl-GT-2558-A (50.8 mg). The $\beta$-galactosidase inhibitory activity of this product is 0.5 IU/mg ($IC_{50}$=500 mcg).

EXAMPLE 11

The yellow oily substance of the acetyl-GT-2558-B obtained in Example 9 is chromatographed for purification repeatedly on a silica gel column, in which the solvent system of hexane-chloroform-methanol (30:30:20) is employed, and recrystallized from a mixture of ethyl acetate and methanol to give colorless fine crystals (12.7 mg). The $\beta$-galactosidase inhibitory activity of this product is 1,640 IU/mg ($IC_{50}$=0.15 mcg).

Fractional enzyme assay of $\beta$-galactosidases (Example 12–18)

EXAMPLE 12

Enzyme solutions are prepared as a mixture of Bovine liver $\beta$-galactosidase solution (A) with *Aspergillus oryzae* $\beta$-galactosidase solution (B) at a rate of 4:0, 3:1, 2:2, 1:3, and 0:4 (V/V), respectively.

To the substrate 0.01M o-nitrophenyl $\beta$-D-galactopyranoside (ONPG) solution (0.5 ml) dissolved in McIlvaine buffer (pH 4.5), the GT-2558-A solution (0.25 ml) dissolved in the said buffer and the above enzyme solution (0.25 ml) are added, and the enzyme reaction is carried out at 37° C. for 15 minutes. Wherein, the concentration of GT-2558-A is $1.9 \times 10^{-4}$M. The reaction is stopped by the addition of 1M sodium carbonate (1 ml), the total volume is adjusted to 10 ml by addition of water (8 ml), and then the enzyme activity (a) is determined from the measurement of the absorbance at 420 nm. Concurrently the said buffer not containing GT-2558-A is added, the enzyme reaction is conducted, the absorbance is measured, and the enzyme activity (t) is determined. In this connection, the difference between t and a value is the amount of $\beta$-galactosidase activity which is inhibited by GT-2558-A ($b=t-a$). Referring to expression of activity, one unit of activity (1 U) is defined as the activity of the enzyme which hydrolyzes 1 $\mu$mole ONPG per minute and liberates o-nitrophenol. In this way the amounts of Bovine liver $\beta$-galactosidase activity (a) and *Aspergillus oryzae* $\beta$-galactosidase activity (b) are determined fractionally.

In Table 1 the results show good accordance between the practical values determined from enzymatic assay and the theoretical ones determined by calculation.

EXAMPLE 13

Enzyme A: Bovine liver $\beta$-galactosidase
Enzyme B: Rat liver $\beta$-galactosidase
Substrate: 0.01M ONPG
Inhibitor: $1.9 \times 10^{-5}$M GT-2558-A
Condition (employed in the reaction): McIlvaine buffer (pH 4.5), 37° C., 15 minutes
Method and the rest are the same as in Example 12. Results are shown in Table 2.

EXAMPLE 14

Enzyme A: Bovine liver $\beta$-galactosidase
Enzyme B: Rat Kidney $\beta$-galactosidase
Substrate: 0.01M ONPG
Inhibitor: $1.9 \times 10^{-4}$M GT-2558-A
Condition: McIlvaine buffer (pH 4.5), 37° C., 15 minutes
Method and the rest are the same as in Example 12. Results are shown in Table 3.

EXAMPLE 15

Enzyme A: Bovine liver $\beta$-galactosidase
Enzyme B: Rat spleen $\beta$-galactosidase
Substrate: 0.01M ONPG
Inhibitor: $1.9 \times 10^{-5}$M GT-2558-A
Condition: McIlvaine buffer (pH 4.5), 37° C., 15 minutes
Method and the rest are the same as in Example 12. Results are shown in Table 4.

EXAMPLE 16

Enzyme A: Bovine liver $\beta$-galactosidase
Enzyme B: *Aspergillus oryzae* $\beta$-galactosidase
Substrate: 0.01M ONPG
Inhibitor: $1.9 \times 10^{-5}$M GT-2558-A
Condition: McIlvaine buffer (pH 7.2), 37° C., 15 minutes
Method and the rest are the same as in Example 12. Results are shown in Table 5.

EXAMPLE 17

Enzyme A: Rat Kidney $\beta$-galactosidase
Enzyme B: *Aspergillus oryzae* $\beta$-galactosidase Substrate : 0.01M ONPG
Inhibitor: $1.9 \times 10^{-6}$M GT-2558-A
Condition: McIlvaine buffer (pH 7.2), 37° C., 15 minutes.
Method and the rest are the same as in Example 12. Results are shown in Table 6.

EXAMPLE 18

Enzyme A: Bovine liver $\beta$-galactosidase
Enzyme B: *E. coli* $\beta$-galactosidase
Substrate: 0.01M ONPG
Inhibitor: $4.8 \times 10^{-5}$M GT-2558-A
Condition: McIlvaine buffer (pH 7.2), 37° C., 15 minutes
Method and the rest are the same as in Example 12. Results are shown in Table 7.

TABLE

| Table No. | Origin of Mixed β-Galactosidase | pH at | Concentration of GT-2558-A (M) | Enzyme activity | above: Practical value below: Theoretical value | | | | |
|---|---|---|---|---|---|---|---|---|---|
| | | | | | 4/0* (U/ml) | 3/1 (U/ml) | 2/2 (U/ml) | 1/3 (U/ml) | 0/4 (U/ml) |
| 1 | A Bovine Liver B Aspergillus oryzae | 4.5 | $1.9 \times 10^{-4}$ | t | 0.32 | 0.28 | 0.25 | 0.22 | 0.19 |
| | | | | | 0.32 | 0.28 | 0.25 | 0.22 | 0.19 |
| | | | | a | 0.00 | 0.04 | 0.08 | 0.14 | 0.19 |
| | | | | | 0.00 | 0.05 | 0.09 | 0.14 | 0.19 |
| | | | | b | 0.32 | 0.24 | 0.17 | 0.08 | 0.00 |
| | | | | | 0.32 | 0.23 | 0.16 | 0.08 | 0.00 |
| 2 | A Bovine Liver B Rat Liver | 4.5 | $1.9 \times 10^{-5}$ | t | 0.16 | 0.18 | 0.20 | 0.22 | 0.24 |
| | | | | | 0.16 | 0.18 | 0.20 | 0.22 | 0.24 |
| | | | | a | 0.01 | 0.07 | 0.13 | 0.19 | 0.24 |
| | | | | | 0.00 | 0.06 | 0.12 | 0.18 | 0.24 |
| | | | | b | 0.15 | 0.11 | 0.07 | 0.04 | 0.00 |
| | | | | | 0.16 | 0.12 | 0.08 | 0.04 | 0.00 |
| 3 | A Bovine Liver B Rat Kidney | 4.5 | $1.9 \times 10^{-4}$ | t | 0.35 | 0.32 | 0.29 | 0.26 | 0.25 |
| | | | | | 0.35 | 0.33 | 0.30 | 0.27 | 0.25 |
| | | | | a | 0.01 | 0.08 | 0.12 | 0.18 | 0.24 |
| | | | | | 0.00 | 0.06 | 0.12 | 0.19 | 0.25 |
| | | | | b | 0.34 | 0.24 | 0.17 | 0.08 | 0.01 |
| | | | | | 0.35 | 0.27 | 0.18 | 0.08 | 0.00 |
| 4 | A Bovine Liver B Rat Spleen | 4.5 | $1.9 \times 10^{-5}$ | t | 0.39 | 0.35 | 0.31 | 0.26 | 0.24 |
| | | | | | 0.39 | 0.36 | 0.32 | 0.28 | 0.24 |
| | | | | a | 0.01 | 0.07 | 0.11 | 0.17 | 0.24 |
| | | | | | 0.00 | 0.06 | 0.12 | 0.18 | 0.24 |
| | | | | b | 0.38 | 0.28 | 0.20 | 0.09 | 0.00 |
| | | | | | 0.39 | 0.30 | 0.20 | 0.10 | 0.00 |
| 5 | A Bovine Liver B Aspergillus oryzae | 7.2 | $1.9 \times 10^{-5}$ | t | 0.30 | 0.28 | 0.27 | 0.26 | 0.26 |
| | | | | | 0.30 | 0.29 | 0.28 | 0.27 | 0.26 |
| | | | | a | 0.00 | 0.06 | 0.12 | 0.19 | 0.25 |
| | | | | | 0.00 | 0.06 | 0.13 | 0.20 | 0.26 |
| | | | | b | 0.30 | 0.22 | 0.15 | 0.07 | 0.01 |
| | | | | | 0.30 | 0.23 | 0.15 | 0.07 | 0.00 |
| 6 | A Rat Kidney B Aspergillus oryzae | 7.2 | $1.9 \times 10^{-6}$ | t | 0.33 | 0.32 | 0.32 | 0.31 | 0.30 |
| | | | | | 0.33 | 0.33 | 0.32 | 0.31 | 0.30 |
| | | | | a | 0.01 | 0.09 | 0.15 | 0.22 | 0.29 |
| | | | | | 0.00 | 0.08 | 0.15 | 0.23 | 0.30 |
| | | | | b | 0.32 | 0.23 | 0.17 | 0.09 | 0.01 |
| | | | | | 0.33 | 0.25 | 0.17 | 0.08 | 0.00 |
| 7 | A Bovine$_2$ Liver B E. coli | 7.2 | $4.8 \times 10^{31\,5}$ | t | 0.21 | 0.23 | 0.25 | 0.27 | 0.29 |
| | | | | | 0.21 | 0.23 | 0.25 | 0.27 | 0.29 |
| | | | | a | 0.01 | 0.07 | 0.14 | 0.21 | 0.29 |
| | | | | | 0.00 | 0.07 | 0.15 | 0.22 | 0.29 |
| | | | | b | 0.20 | 0.16 | 0.11 | 0.06 | 0.00 |
| | | | | | 0.21 | 0.16 | 0.10 | 0.05 | 0.00 |

Notes
A: the enzyme which is not completely inhibited GT-2558-A of the shown concentrations
B: the enzyme which is completely inhibited by GT-2558-A of the shown concentrations
t: the β-galactosidase activity measured in the absence of GT-2558-A (total activity)
a: the β-galactosidase activity measured in the presence of GT-2558-A (the enzyme activity of A)
b: b = t − a, the difference between t and a, the amount of the enzyme activity inhibited by GT-2558-A (the enzyme activity of B)
*: B/A, the mixture rate of the enzyme A and the enzyme B

EXAMPLE 19

Cow's milk (1000 ml) was slowly stirred at 30° C., to which 500 mg of β-galactosidase (produced by *Aspergillus oryzae*) (lactose hydrolyzing potency: 20 U/mg) was added. A portion (100 ml each) of the mixture was collected at pre-determined intervals, and GT-2558-A (2 mg) was added thereto to stop the enzymatic reaction to give a partially lactose-hydrolyzed milk. Table 8 indicates the rate (%) of hydrolysis of lactose and the result of sweetness test by testers A–D. As seen from the table, the sweetness of milk can freely be controlled by addition of the inhibitor at an appropriate time.

TABLE 8

| Time (min) | 10 | 20 | 30 | 60 | 120 | 180 | 240 |
|---|---|---|---|---|---|---|---|
| Rate (%) of Hydrolysis* | 15.4 | 24.8 | 32.3 | 48.6 | 67.0 | 79.9 | 90.1 |
| Tester** A | − | − | ± | + | ++ | +++ | +++ |
| B | ± | − | + | + | ++ | +++ | +++ |
| C | ± | − | ± | + | + | ++ | +++ |
| D | ± | ± | ± | + | ++ | +++ | +++ |

*The rate of hydrolysis of lactose was determined by conventional quantitative analysis with glucose oxidase on glucose released from lactose.
**Result of the test was represented by the following 5 degrees compared with the taste of milk.
−: no change appreciable
±: slightly sweet
+: sweet and agreeable
++: sweet but disagreeable
+++: too sweet and unacceptable

EXAMPLE 20

Preparation of Sweetening Agent from Skim Milk:
Dry skim milk (200 g) was suspended in water so as to give 20% suspension (1L), which was slowly stirred at 30° C. β-Galactosidase (1 g) (produced by *Aspergillus oryzae*) was added thereto, and a portion of the mixture (100 ml each) was collected at predetermined intervals and treated with 4 mg GT-2558-A. Table 9 indicates the rate (%) of hydrolysis of lactose and the result of sweetness test by tasters A–D. As shown in Table 9, skim milk can be converted into sweetening agents having appropriate sweetness.

TABLE 9

| Time (hr) | | 0.5 | 1 | 1.5 | 2 | 3 | 4 |
|---|---|---|---|---|---|---|---|
| Rate (%) of Hydrolysis* | | 27.4 | 39.2 | 50.1 | 59.2 | 70.6 | 78.9 |
| Taster** | A | — | ± | + | + | ++ | ++ |
| | B | ± | + | + | + | ++ | ++ |
| | C | ± | ± | ± | + | ++ | ++ |
| | D | ± | ± | + | + | ++ | ++ |

*Determined in the same manner as in Example 19.
**Represented by the following 4 degrees compared with the taste of 20% skim milk suspension.
—: no change appreciable
±: slightly sweet
+: sweet
++: very sweet

What is claimed is:

1. GT-2558-A with the following properties or a pharmaceutically acceptable salt thereof:
   a. m.p.
      106°–108° C.
   b. Molecular weight (mass spectrum)
      Maximum mass m/e=302
   c. Elemental analysis
      Found: C,41.34; H,6.16; N,7.43; O,45.06 (%)
   d. IR
      $\nu_{max}^{KBr}$ 3400, 2900, 1640, 1565, 1505, 1455, 1415, 1360, 1300, 1270, 1160, 1110, 1075, 1035, 955, 930, 890, 855, 795 cm$^{-1}$
   e. NMR
      FIG. 1 and FIG. 2
   f. β-Galactosidase inhibitory activity

| Enzyme | pH at | Origin | IC$_{50}$ | |
|---|---|---|---|---|
| Taka β-galactosidase | 5.0 | Aspergillus oryzae(Sankyo) | 0.0018 | mcg |
| Taka β-galactosidase | 4.5 | Aspergillus oryzae(Sankyo) | 0.0045 | |
| Galantase | 4.5 | Aspergillus oryzae(Tokyo Tanabe) | 0.0045 | |
| Bovine β-galactosidase | 7.2 | Bovine liver (Sigma) | 26.6 | | g. Specific β-galactosidase inhibitory activity
      136,700 IU/mg (IC$_{50}$ 0.0018 mcg).

Figure 4:
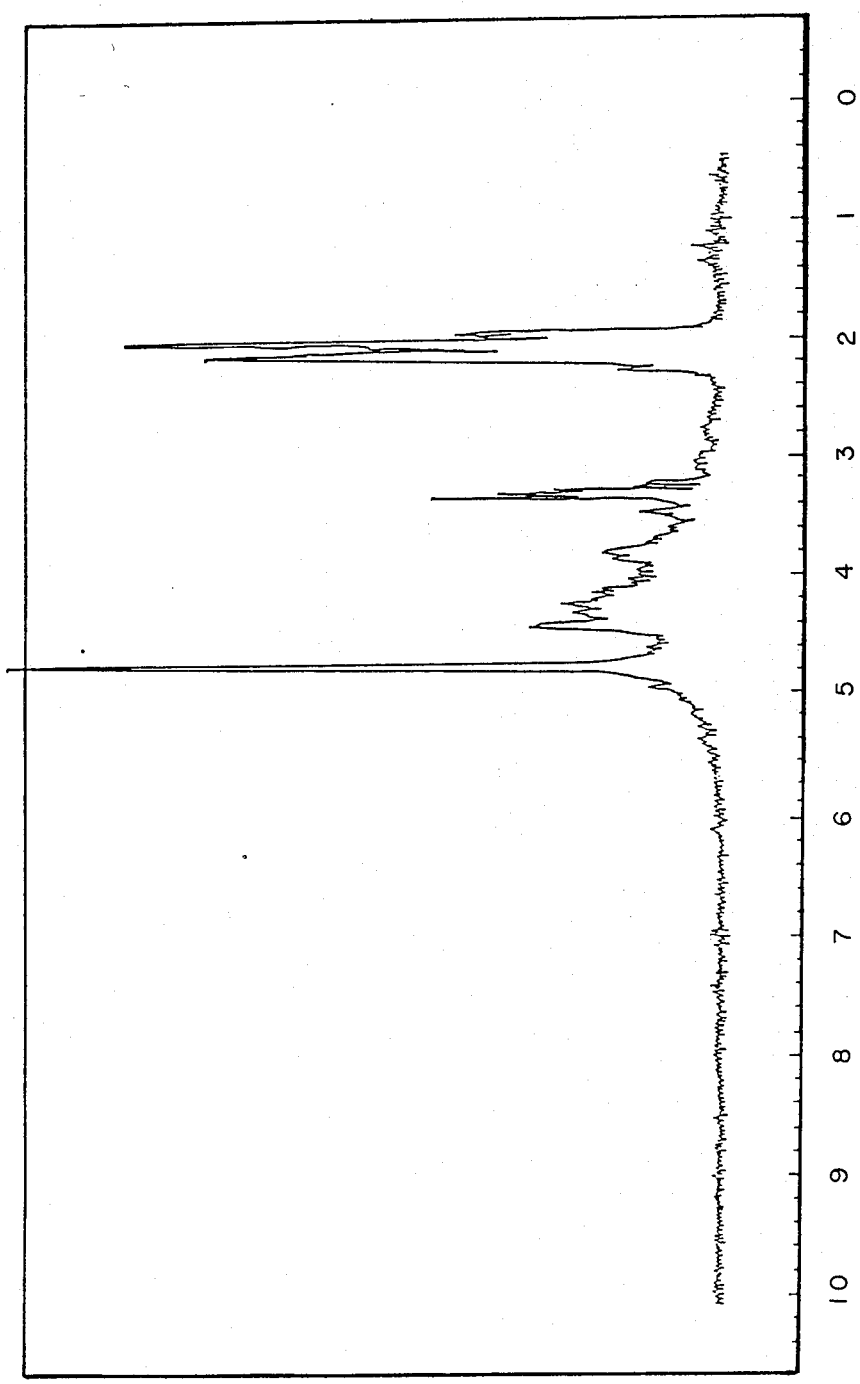
FIG. 4 shows the NMR spectrum of the acetyl-GT-2558-A measured in heavy methanol.

2. Acetyl-GT-2558-A with the following properties or a pharmaceutically acceptable salt thereof:
   a. Nature
      Colorless fine crystals (recrystallized from benzene-methanol)
   b. Solubility
      Soluble in methanol, ethanol, chloroform, dioxane, and water, slightly soluble in ethyl acetate, and insoluble or hardly soluble in carbon tetrachloride and benzene
   c. Color reaction
      Ninhydrin reaction test    positive
      Ammoniac silver nitrate reaction test    positive
   d. m.p. and decom.p.
      m.p. 41° C.; decomp.p. 149°–153° C.
   e. Specific rotation
      $[\alpha]_D^{24}$ +29.6° (c 1.0 methanol)
   f. Molecular weight (mass spectrum)
      Maximum mass m/e=491 (M+1)
   g. Elemental analysis
      Found: C,51.30; H,6.27; N,5.65; O,36.78 (%)
   h. UV
      No characteristic absorption
   i. IR
      $\nu_{max}^{KBr}$ 3430, 2920, 1745, 1630, 1435, 1390, 1370, 1245, 1090, 1040, 820, 760 cm$^{-1}$
   j. NMR
      FIG. 4
   k. Specific β-galactosidase inhibitory activity
      0.5 IU/mg (IC$_{50}$ 500 mcg).

3. Acetyl-GT-2558-B with the following properties or a pharmaceutically acceptable salt thereof:
   a. Nature
      Colorless fine crystals (recrystallized from ethyl acetate-methanol)
   b. Solubility
      Soluble in methanol, ethanol, and water, slightly soluble in ethyl acetate and chloroform, and insoluble or hardly soluble in carbon tetrachloride and benzene
   c. Color reaction
      Ninhydrin reaction test    positive
      Ammoniac silver nitrate reaction test    positive
   d. m.p. and decom.p.
      m.p. 76°–78° C; decomp.p. 161°–163° C.
   e. Specific rotation
      $[\alpha]_D^{24}$ +13.8° (c 1.0 methanol)
   f. Molecular weight (mass spectrum)
      Maximum mass m/e=429 (M+1)
   g. Elemental analysis
      Found: C,46.58; H,60.58; N,6.56;038.51 (%)
   h. UV
      No characteristic absorption
   i. IR
      $\nu_{max}^{KBr}$ 3410, 2930, 2735, 2360, 1640, 1550, 1435, 1380, 1245, 1195, 1115, 1090, 1045, 875, 815 cm$^{-1}$
   j. NMR
      FIG. 3
   k. Specific β-galactosidase inhibitory activity
      1,640 IU/mg (IC$_{50}$ 0.15 mcg).

4. Method for producing GT-2558-A as defined in claim 1, which comprises culturing a GT-2558-A producing strain of *Streptomyces lydicus* PA-5726, FERM BP-61 on a culture medium, under aerobic conditions at a temperature of 20° to 40° C. for about 20 to 80 hours and recovering GT-2558-A from the culture broth.

* * * * *